United States Patent [19]

Capps et al.

[11] 4,207,320
[45] Jun. 10, 1980

[54] AMINO-SUBSTITUTED IMIDAZO[1,2-A:3,4-A']DIQUINOLIN-15-IUM SALTS COMPOSITIONS AND METHOD OF USE

[75] Inventors: David B. Capps, Ann Arbor; Mario M. Angelo, Ypsilanti; Townley P. Culbertson, Ann Arbor, all of Mich.

[73] Assignee: Warner-Lambert Company, Morris Plains, N.J.

[21] Appl. No.: 937,234

[22] Filed: Aug. 28, 1978

[51] Int. Cl.² .......................................... A61K 31/535
[52] U.S. Cl. ........................... 424/248.56; 260/244.4; 424/258; 544/80; 544/125; 546/52
[58] Field of Search ............ 260/286 Q, 288 CF, 244.4; 544/80, 125; 424/258, 248.56; 546/52

[56] References Cited

U.S. PATENT DOCUMENTS 3,253,986 5/1966 Franklin .............................. 167/53

OTHER PUBLICATIONS

Burger, "Medicinal Chemistry", 2nd Ed., Interscience Publishers, Inc., N.Y., (1960), p. 1055.
Morrison, R. T., and R. N. Boyd, "Organic Chemistry", Allyn and Bacon, Inc., Boston, 1976, p. 734.
Brown, B. R. and E. H. Wild, "J. Chem. Soc.", (1956), pp. 1158-1163.

*Primary Examiner*—Donald G. Daus
*Assistant Examiner*—Lisa Jones
*Attorney, Agent, or Firm*—Albert H. Graddis; George M. Kaplan; Frank S. Chow

[57] ABSTRACT

Amino-substituted imidazo[1,2-a:3,4-a']diquinolin-15-ium salts having the formula I:

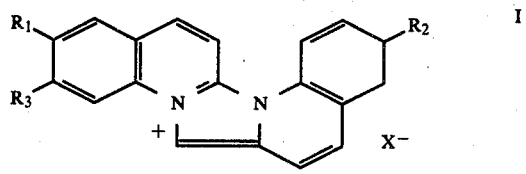

wherein
  $R_1$ is hydrogen, lower alkyl, $C_4$–$C_6$ cycloalkyl, di(-lower alkyl)amino, 1-azetidinyl, 1-pyrrolidinyl, 1-piperidinyl, methyl-1-pyrrolidinyl, methyl-1-piperidinyl, 4-morpholinyl or 2,2-dimethylhydrazino;
  $R_2$ is hydrogen, lower alkyl, lower alkylamino, di(-lower alkyl)amino, $C_4$–$C_6$ cycloalkylamino, lower alkoxy(lower alkyl)amino, 1-azetidinyl, 1-pyrrolidinyl, 1-piperidinyl, methyl-1-pyrrolidinyl, methyl-1-piperidinyl, hexahydro-1H-azepin-1-yl, 4-morpholinyl, benzylamino, N-methylbenzylamino or 2-phenylethylamino;
  $R_3$ is hydrogen or methyl;
  X is an anion;

with the proviso that at least one of $R_1$ and $R_2$ is other than hydrogen, lower alkyl or $C_4$–$C_6$ cycloalkyl; and with the further proviso that when $R_2$ is dimethylamino, at least one of $R_1$ and $R_3$ is other than hydrogen, and intermediates used in the preparation thereof are disclosed. The compounds of the invention are prepared by amination of the corresponding chloro or fluoro-substituted imidazo [1,2-a:3,4-a']diquinolin-15-ium salts; either the halo substituted intermediates or the amino substituted salts may be further treated, typically using ion exchange techniques to obtain a variety of physiologically acceptable amino-substituted [1,2-a:3,4-a']diquinolin-15-ium salts which exhibit antifungal activity.

33 Claims, No Drawings

AMINO-SUBSTITUTED IMIDAZO[1,2-A:3,4-A']DIQUINOLIN-15-IUM SALTS COMPOSITIONS AND METHOD OF USE

BACKGROUND OF THE INVENTION

1. Field of the Invention

The present invention relates to amino-substituted imidazo[1,2-a:3,4-a']diquinolin-15-ium salts which exhibit antifungal activity.

2. Description of the Prior Art

Imidazo[1,2-a:3,4-a']diquinolin-15-ium bromide is described by Brown, et al. in J. Chem. Soc. 1956:1158–1163. No utility for this compound is disclosed by Brown, et al.

Substituted or unsubstituted imidazo[1,2-a:3,4-a']diquinolin-15-ium salts having antiparasitic activity are disclosed in U.S. Pat. No. 3,253,986. A possible methyl substituent on the three or ten position of the imidazo diquinoline ring is disclosed. Compositions containing the compounds described are also stated to exhibit antibacterial, antiamebic and antitrichomonal activity.

The compounds of the instant invention differ from those disclosed in aforementioned references in that (1) an amino substituent is present on either the three and/or ten position; and (2) fungicidal activity is claimed. Additionally, the intermediates used to prepare the amino-substituted final compounds of this invention differ from the compounds of the above mentioned references in that no fluoro or chloro substituents are present on the prior art compounds.

DESCRIPTION OF THE PARTICULAR EMBODIMENTS

The present invention relates to novel amino-substituted imidazo[1,2-a:3,4-a']diquinolin-15-ium salts having the general formula I:

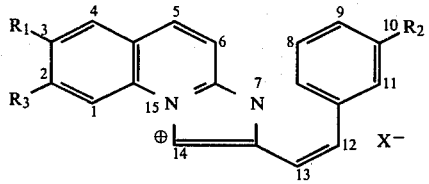

wherein
$R_1$ is hydrogen, lower alkyl, $C_4$–$C_6$ cycloalkyl, di(lower alkyl)amino, 1-azetidinyl, 1-pyrrolidinyl, 1-piperidinyl, methyl-1-pyrrolidinyl, methyl-1-piperidinyl, 4-morpholinyl or 2,2-dimethylhydrazino;

$R_2$ is hydrogen, lower alkyl, lower alkylamino, di(lower alkyl)amino, $C_4$–$C_6$ cycloalkylamino, lower alkoxy(lower alkyl)amino, 1-azetidinyl, 1-pyrrolidinyl, 1-piperidinyl, methyl-1-pyrrolidinyl, methyl-1-piperidinyl, hexahydro-1H-azepin-1-yl, 4-morpholinyl, benzylamino, N-methylbenzylamino or 2-phenylethylamino;

$R_3$ is hydrogen or methyl;
X is an anion;
with the proviso that at least one of $R_1$ and $R_2$ is other than hydrogen, lower alkyl or $C_4$–$C_6$ cycloalkyl (i.e., at least one of $R_1$ and $R_2$ is one of the above-named nitrogen-containing substituents); and with the further proviso that when $R_2$ is dimethylamino, at least one of $R_1$ and $R_3$ is other than hydrogen (i.e., at least one of $R_1$ and $R_3$ is one of the above-named substituents other than hydrogen).

The preferred compounds of the invention are those having the formula I wherein $R_1$ is hydrogen, methyl, ethyl, n-butyl, t-butyl, dimethylamino, 1-pyrrolidinyl or methyl-1-piperidinyl; $R_2$ is hydrogen, methyl, ethyl, n-butyl, t-butyl, dimethylamino, (N-methyl)butylamino, 1-pyrrolidinyl, 1-piperidinyl and methyl-1-piperidinyl; $R_3$ is hydrogen; X is a chloride, iodide or p-toluenesulfonate; with the proviso that at least one of $R_1$ and $R_2$ is other than hydrogen, methyl, ethyl, n-butyl or t-butyl (i.e. at least one of $R_1$ and $R_2$ is one of the above-named nitrogen-containing substituents); and with the further proviso that when $R_2$ is dimethylamino, $R_1$ is other than hydrogen (i.e., $R_1$ is one of the above-named substituents other than hydrogen).

The compounds of the invention having the formula I are prepared by reacting a compound having the formula II:

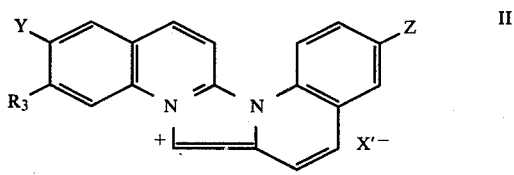

wherein
Y is hydrogen, lower alkyl, $C_4$–$C_6$ cycloalkyl, fluoro or chloro;
Z is hydrogen, lower alkyl, fluoro or chloro; with the proviso that at least one of Y and Z is fluoro or chloro, preferably fluoro;
$R_3$ is hydrogen or methyl; and X' is an anion; with a solvent solution of an appropriate amine at a temperature of from about 20° C. to about 200° C. Suitable amine reactants include lower alkyl amines, di(lower alkyl)amines, lower alkoxy(lower alkyl)amines, azetidine, pyrrolidine, piperidine, methylpyrrolidine (especially 2- or 3-methylpyrrolidine), methylpiperidine (especially 4-methylpiperidine), morpholine, 2,2-dimethylhydrazine, $C_4$–$C_6$ cycloalkylamines, hexahydro-1H-azepine, benzylamine, N-methylbenzylamine, 2-phenethylamine, and the like. Solvents which may be used in the amination reaction include tertiary amides such as dimethylformamide and N-methyl-2-pyrrolidinone; alcohols such as methanol, ethanol and ethyleneglycol; dimethylsulfoxide; and an excess of the above-mentioned amine reactants; and mixtures thereof. The temperature and time of the amination reaction are not critical and may be varied considerably depending upon the choice of reactants. For example, the amination reaction may be conducted at from about 20° C. to about 200° C. for from about 30 minutes to about 48 hours. In the case of one particular amine reactant, namely azetidine, room temperature is preferred for the amination reaction and the reaction can take up to three weeks in time. Generally, for other reactants, a temperature range of from about 130° C. to about 190° C. is preferred.

Intermediate compounds II are obtained by reacting an appropriately substituted quinoline compound III with an appropriately substituted quinaldine compound IV:

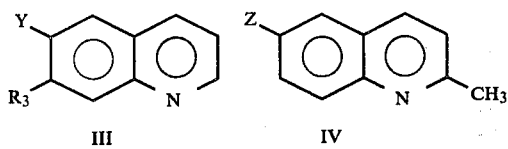

wherein Y, Z and R₃ are as defined above for compound II; in the presence of an inert organic solvent containing iodine, following the procedure described in U.S. Pat. No. 3,253,986. The chloro- or fluoro-substituted intermediates from the last mentioned reaction are obtained in the form of the iodide salt V:

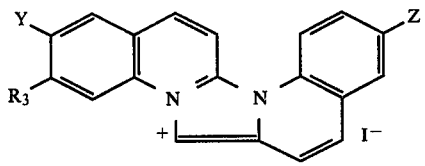

wherein Y, Z and R₃ are as defined above for formula II. Compounds V can be converted to any other desired anion salt in accordance with known procedures such as ion exchange either before or after the amination reaction. Thus, for example, the iodide salt V may be converted to the corresponding p-toluenesulfonate salt smoothly by reaction with methyl p-toluenesulfonate at from about 0° C. to about 50° C., with liberation of methyl iodide. This is a particularly significant reaction since it makes possible the recovery of the iodine reagent used to form the diquinoline ring structure. The p-toluenesulfonates may be converted to the chloride salts by passage in solution over a column of an anion exchange resin (Amberlite IRA-410) in the chloride ion form. In an alternative procedure, the p-toluenesulfonates may be converted to the hydroxide salt by passage in solution over a strongly basic anion exchange resin (Amberlite IRA-410) in the hydroxide ion form; other salts may then be formed from the hydroxide salt by direct reaction with other acids. If desired, soluble salts such as the chlorides may be converted to less soluble salts by metathesis, i.e., by reaction of the former with the sodium or potassium salt of the less soluble acid. In another variation of the salt formation reaction, the iodides may be converted to the chlorides by a reaction with a large excess of a concentrated aqueous solution of a soluble chloride such as sodium chloride.

The substituted quinoline compounds III are prepared by reacting a substituted aniline with glycerol in the presence of sulfuric acid and sodium 3-nitrobenzenesulfonate. And the substituted quinaldine compounds IV are prepared by reacting a substituted aniline with crotonaldehyde in the presence of sulfuric acid and sodium 3-nitrobenzenesulfonate.

Thus, according to the above described procedures, intermediates having the formula II:

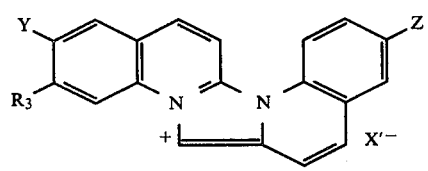

wherein Y, Z and R₃ are as defined above in formulas III and IV and X' is an anion are obtained.

As examples of some of the many suitable anions X and X' contemplated within the scope of this invention, there may be mentioned the chloride, bromide, iodide, hydroxide, bisulfite, bisulfate, hemisulfate, perchlorate, acetate, palmitate, stearate, hemipamoate, decanesulfonate, hydroxy-naphthoate, dodecylsulfate, cyclohexanesulfamate, trichlorophenoxide, dihydroxyisonicotinate, bromonaphthoxide, hemiadipate, p-toluenesulfonate, lactate, citrate, benzoate, salicylate, hemi-(5,5-thiodisalicylate), 3,5-dichlorosalicylate, taurocholate, dioctylsulfosuccinate, 5-acetyl-8-hydroxy quinoline and the like. Among the above-mentioned anions, the iodide and hydroxide salts are most useful as intermediate compounds suitable for conversion to other anions which are more soluble and often more useful for physiological end uses. Among the physiologically acceptable anions, the chloride and p-toluenesulfonate salts are preferred, with the chloride salts being the most preferred.

In the above mentioned formulas I through V, it is intended that lower alkyl and the lower alkyl portion of lower alkoxy be meant to include one to six carbon, straight or branched chains such as methyl, ethyl, propyl, isopropyl, butyl, secondary butyl, tertiary butyl, hexyl, and the like; and $C_4$–$C_6$ cycloalkyl is meant to include cyclobutyl, cyclopentyl and cyclohexyl.

The novel compounds of this invention having the formula I wherein $R_1$, $R_2$ and $R_3$ are as defined above and X is a physiologically acceptable anion and the non-toxic, pharmaceutically acceptable acid addition salts thereof have been found to exhibit anti-fungal activity against fungi including *Candida albicans, Candida stellatoidea, Candida tropicalis, Candida krusei, Candida gulliermondi, Candida parapsilosis, Geotrichum candidum, Trichophyton mentagrophytes, Trichophyton tonsurans, Trichophyton terrestre, Microsporum nanum, Microsporum gypseum* and *Microsporum vanbreuseghemii*. Minimum inhibitory concentrations falling with the range of from about 0.64 to about 200 micrograms/milliliters (μg./ml.) are obtained when the above described compounds are evaluated in the in vitro Broth Tube Dilution Test, which is performed as follows:

BROTH TUBE DILUTION TEST

Minimal Inhibitory Concentration (MIC)

The test compounds are serially diluted in pure dimethylformamide, giving a concentration of 4000, 800, 160 and 32 micrograms/milliliters(μg./ml.). A further dilution (typically a 2-fold or a 5-fold dilution) is made from each of the above serial dilutions into tubes containing 9.4 ml. BactoSabouraud Dextrose Broth, resulting in a set of broth tubes with specific final drug concentrations for which activity is to be determined. Each of the broth tubes is then inoculated with 0.5 ml. of a stock suspension of the same test organism. After inoculation, all of the tubes are incubated at 28° C. The tubes are read 48 hours to 7 days post inoculation, depending on the organism being tested. The lowest concentration of test compound at which growth of the organism is prevented in the broth tubes is taken as the minimal inhibitory concentration (MIC). The Broth+Serum Dilution Test is performed in the same manner as the Broth Tube Dilution Test except that the liquid medium consists of 50% BactoSabouraud Dextrose Broth and 50% normal calf serum from citrated blood.

BROTH TUBE DILUTION TEST

Minimal Fungicidal Concentrations (MFC)

For a determination of fungicidal activity, the broth tubes described above are incubated at 28° C. for 48 hours and then serially diluted 1:100 into Bacto-Sabouraud Dextrose Broth and incubated again for 48 hours. The tubes are then read and the lowest concentration of test compound for which there is no growth of the organism in the broth tube is taken as the minimal fungicidal concentration (MFC).

Test results with representative compounds of this invention are listed below:

A. 10-(1,1-dimethylethyl)-3-(1-pyrrolidinyl)imidazo[1,2-a:3,4-a']-diquinolin-15-ium chloride (compound of Example 7)

| TEST ORGANISM | μg./ml. at 28° C. | |
|---|---|---|
| | MIC[1] | MFC[2] |
| C. albicans | 10 | 10 |
| C. stellatoidea | 2.61 | 5 |
| C. tropicalis | >10 | >10 |
| Geotrichum candidum | 10 | >10 |
| C. krusei | 10 | 10 |
| C. guilliermondi | 2.5 | 2.5 |
| C. parapsilosis | 10 | >10 |

B. 10-ethyl-3-(1-pyrrolidinyl)imidazo[1,2-a:3,4-a']diquinolin-15-ium chloride (compound of Example 26)

| TEST ORGANISM | μg./ml. at 28° C. | |
|---|---|---|
| | MIC[1] | MFC[2] |
| C. albicans | 2.5 | 2.5 |
| C. stellatoidea | 1.25 | 5 |
| C. tropicalis | 10 | >10 |
| Geotrichum candidum | 5 | >10 |
| C. krusei | 2.5 | 2.5 |
| C. guilliermondi | 10 | >10 |
| C. parapsilosis | 5 | >10 |

[1]minimal inhibitory concentration at 72 hours
[2]minimal fungicidal concentration, 24 hours later Thus, the novel compounds of this invention having the formula I as described above are useful as antifungal agents and can be administered orally or topically to mammals such as mice, guinea pigs and the like, afflicted with fungal diseases. The compounds of this invention are especially useful since they exhibit antifungal activity within a very short period of time. The effective dosage range is from about 0.1 to about 100 mg/kg of body weight for the treatment of a fungal disease.

Among the dosage forms which can be used for oral administration are, for example, tablets or capsules which are well known in the pharmacist's art. Among the dosage forms which can be used for topical application are, for example, powders, ointments, and creams. In these dosage forms, the active ingredients at levels of from about 1% to 10% by weight are blended together with a selected vehicle such as polyethylene glycol 400 and applied to sites afflicted with the susceptible organisms. The methods for the compounding of these topical applications are well known to the pharmacist's art.

The compounds of this invention having the formula I have also been found to be active against the bacteria Streptococcus pyogenes, Staphylococcus aureus, Streptococcus faecalis, Escherichia coli and Serratia marcescens.

The following examples are included to further illustrate the invention:

EXAMPLE 1

10-Methyl-3-(1-pyrrolidinyl)imidazo[1,2-a:3,4-a']diquinolin-15-ium Chloride

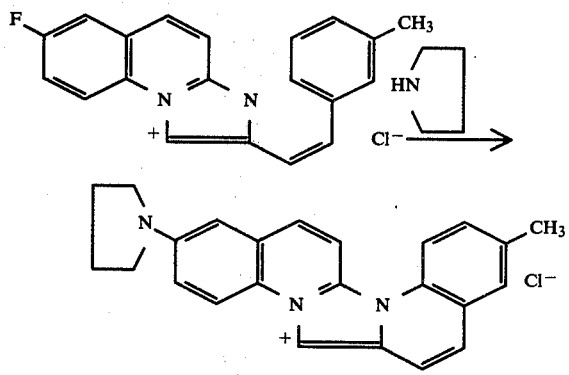

A stirred mixture of 219.5 g. of 3-fluoro-10-methylimidazo[1,2-a:-3,4-a']diquinolin-15-ium chloride trihydrate and 580 ml. of N-methyl-2-pyrrolidinone is heated to 150° C. and 144 ml. of pyrrolidine is added over a 2 minute period. The mixture is heated and stirred at reflux (132°–140° C.) for 40 minutes, allowed to cool, and then is diluted with 2 l. of ethyl acetate. The precipitated solid is collected by filtration, washed with ethyl acetate, dried and dissolved in 1.6 l. of methanol. The methanol solution is treated with 20 g. of activated charcoal and filtered. The filtrate is passed over a column of 1 l. of IRA-410 anion exchange resin (Cl⁻ form, suspended in methanol) over a period of 3 hours. The eluate is evaporated at reduced pressure to give a residue of 10-methyl-3-(1-pyrrolidinyl)-imidazo[1,2-a:3,4-a']diquinolin-15-ium chloride; m.p. 245°–320° C. (dec.) after crystallization from dimethylformamide and from 2-propanol/acetonitrile.

EXAMPLE 2

3-(1-Piperidinyl)-10-propylimidazo[1,2-a:3,4-a']diquinolin-15-ium Iodide

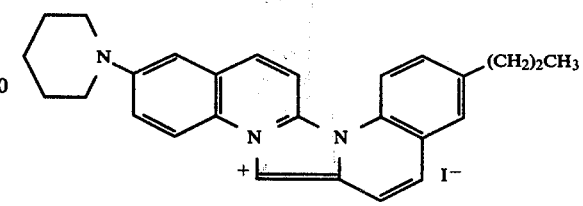

A stirred mixture of 3.62 g. of 3-fluoro-10-propylimidazo[1,2-a:3,4-a']diquinolin-15-ium iodide, 20 ml. of dimethylformamide and 2.0 ml. of piperidine is heated at 72° C. for 94 hours, then evaporated at reduced pressure. The residue is dissolved in methanol along with 2.0 g. of triethylamine hydroiodide. The solution is diluted with water and the resulting precipitate is collected by filtration and suspended in 125 ml. of 0.5% triethylamine hydroiodide. The solid 3-(1-piperidinyl)-10-propylimidazo[1,2-a:3,4-a']diquinolin-15-ium iodide is collected by filtration, triturated with 2-propanol and dried; m.p. 148°–153° C.

EXAMPLE 3

3-Dimethylamino-10-ethylimidazo[1,2-a:3,4-a']diquinolin-15-ium Iodide.

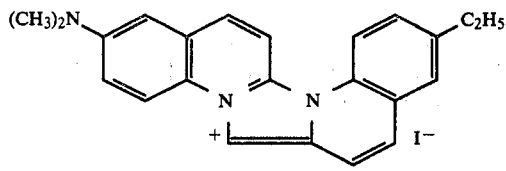

A mixture of 2.28 g. of 10-ethyl-3-fluoroimidazo[1,2-a:3,4-a']-diquinolin-15-ium iodide, 100 ml. of methanol and 2.0 g. of dimethylamine is stirred and heated in a pressure vessel for 12 hours at 190° C., then evaporated at reduced pressure. The residue is crystallized from methanol-ethyl acetate and the resulting crystalline solid is suspended in 1% aqueous triethylamine hydroiodide, The solid is collected by filtration and dissolved in methanol. The methanol solution is treated with activated charcoal, filtered and diluted with 2-propanol to crystallize 3-dimethylamino-10-ethylimidazo[1,2-a:3,4-a']diquinolin-15-ium iodide which is collected by filtration and dried; m.p. 295°-304° C.

In a similar manner, by substituting an equivalent amount of the appropriate 3-fluoroimidazo[1,2-a:3,4-a']diquinolin-15-ium iodide for the 10-ethyl-3-fluoroimidazo[1,2-a:3,4-a']diquinolin-15-ium iodide in the above example, the following products are obtained:
(a) 3-Dimethylaminoimidazo[1,2-a:3,4-a']diquinolin-15-ium Iodide; m.p. 286°-291° C., from 1% methanolic triethylamine hydroiodide.
(b) 3-Dimethylamino-10-methylimidazo[1,2-a:3,4-a']-diquinolin-15-ium Iodide; m.p. 319°-321° C., from methanol.
(c) 10-Butyl-3-dimethylaminoimidazo[1,2-a:3,4-a']diquinolin-15-ium Iodide; m.p. 250°-258° C. (dec.), from methanol/ether.
(d) 3-Dimethylamino-10-(1-methylethyl)imidazo[1,2-a:3,4-a']diquinolin-15-ium Iodide; m.p. 290°-295° C., from methanol/ether.
(e) 3-Dimethylamino-10-(1,1-dimethylethyl)imidazo[1,2-a:3,4-a']diquinolin-15-ium Iodide; m.p. 360° C., from methanol/ether.

EXAMPLE 4

3-(1-Azetidinyl)-10-propylimidazo[1,2-a:3,4-a']diquinolin-15-ium Iodide.

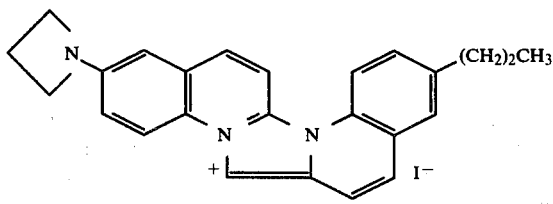

A mixture of 4.83 g. of 3-fluoro-10-propylimidazo[1,2-a:3,4-a']diquinolin-15-ium iodide, 25 ml. of dimethylformamide and 2.0 ml. of azetidine is allowed to stand at room temperature for 7 days. An additional 0.5 ml. of azetidine is added and the mixture is allowed to stand an additional 14 days, then is cooled to 0°-5° C. The precipitate of 3-(1-azetidinyl)-10-propylimidazo[1,2-a:3,4-a']diquinolin-15-ium iodide is collected by filtration, washed with water and dried; m.p. 268°-274° C. after crystallization from methanol and from dimethylformamide/2-propanol.

In a similar manner, by substituting an equivalent amount of 10-ethyl-3-fluoroimidazo[1,2-a:3,4-a']diquinolin-15-ium iodide for the 3-fluoro-10-propylimidazo[1,2-a:3,4-a']diquinolin-15-ium iodide in the above example, the following product is obtained:
(a) 3-(1-Azetidinyl)-10-ethylimidazo[1,2-a:3,4-a']diquinolin-15-ium Iodide; m.p. 246°-256° C., from methanol.

EXAMPLE 5

10-(1,1-Dimethylethyl)-3-(1-pyrrolidinyl)imidazo[1,2-a:3,4-a']diquinolin-15-ium Iodide.

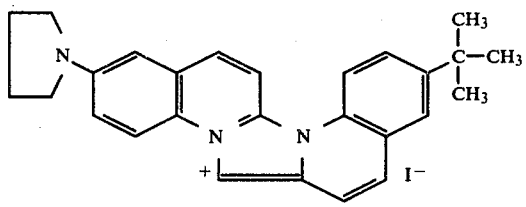

A mixture of 141 g. of 10-(1,1-dimethylethyl)-3-fluoroimidazo[1,2-a:3,4-a']diquinolin-15-ium iodide, 725 ml. of N-methyl-2-pyrrolidinone and 75 ml. of pyrrolidine is stirred and heated at reflux for 1 hour, then cooled and diluted with 3.6 l. of ethyl acetate. The resulting precipitate of 10-(1,1-dimethylethyl)-3-(1-pyrrolidinyl)imidazo[1,2-a:3,4-a']diquinolin-15-ium iodide is collected by filtration, washed with water and dried; m.p. >360° C.

In a similar manner, by substituting equivalent amounts of the appropriate 3-fluoroimidazo[1,2-a:3,4-a']diquinolin-15-ium iodide and the appropriate amine for the above reactants, the following products are obtained:
(a) 10-Methyl-3-(1-pyrrolidinyl)imidazo[1,2-a:3,4-a']diquinolin-15-ium Iodide; m.p. 322°-327° C., from dimethylformamide/methanol.
(b) 10-Propyl-3-(1-pyrrolidinyl)imidazo[1,2-a:3,4-a']diquinolin-15-ium Iodide; m.p. 266°-272° C. (dec.), from N-methyl-2-pyrrolidinone.
(c) 10-Ethyl-3-(1-pyrrolidinyl)imidazo[1,2-a:3,4-a']diquinolin-15-ium Iodide; m.p. 315°-325° C., from N-methyl-2-pyrrolidinone/ethyl acetate.
(d) 10-Ethyl-3-(1-piperidinyl)imidazo[1,2-a:3,4-a']diquinolin-15-ium Iodide; m.p. 272°-276° C., from methanol.
(e) 10-(1,1-Dimethylethyl)-3-(1-piperidinyl)imidazo[1,2-a:3,4-a']diquinolin-15-ium Iodide; m.p. 285°-300° C., from N-methyl-2-pyrrolidinone/ethyl acetate.
(f) 3-(1-Pyrrolidinyl)imidazo[1,2-a:3,4-a']diquinolin-15-ium Iodide; m.p. 312°-320° C., from methanol.
10-Methyl-3-(1-piperidinyl)imidazo[1,2-a:3,4-a']diquinolin-15-ium Iodide; dec. at 310° C.-320° C., from N-methyl-2-pyrrolidinone/ethyl acetate.
(h) 3-(1-Piperidinyl)imidazo[1,2-a:3,4-a']diquinolin-15-ium Iodide; dec. at 280° C.-290° C. from N-methyl-2-pyrrolidinone/ethyl acetate.

EXAMPLE 6

10-(1,1-Dimethylethyl)-3-(1-pyrrolidinyl)imidazo[1,2-a:3,4-a']diquinolin-15-ium p-Toluenesulfonate.

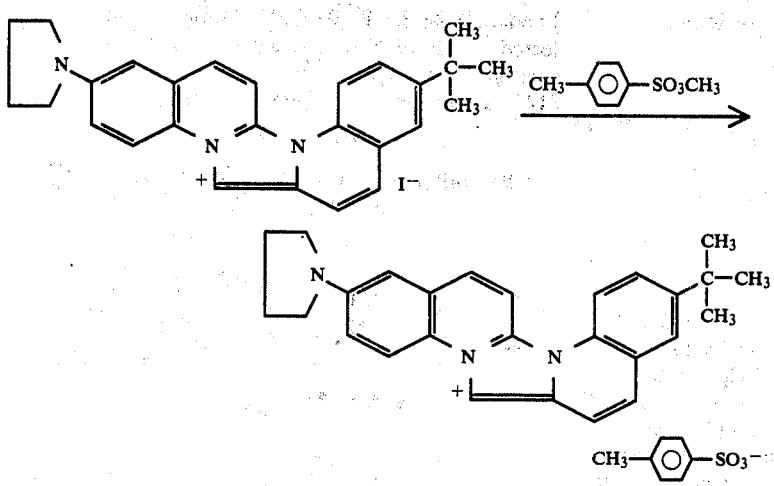

A mixture of 140 g. of 10-(1,1-dimethylethyl)-3-(1-pyrrolidinyl)-imidazo[1,2-a:3,4-a']diquinolin-15-ium iodide, 1.4 l. of dimethylformamide and 100 g. of methyl p-toluenesulfonate is stirred at 50° C. for 1 hour while the system is flushed with nitrogen. The mixture is cooled and diluted with 1.4 l. of ethyl acetate. The resulting precipitate of 10-(1,1-dimethylethyl)-3-(1-pyrrolidinyl)imidazo[1,2-a:3,4-a']diquinolin-15-ium p-toluenesulfonate is collected by filtration and dried; m.p. 264°-275° C.

In a similar manner, from the corresponding iodide salt, the following p-toluenesulfonate salts are obtained:

(a) 10-Methyl-3-(1-pyrrolidinyl)imidazo[1,2-a:3,4-a']diquinolin-15-ium p-Toluenesulfonate; m.p. 279°-284° C., from dimethylformamide/ethyl acetate.

(b) 10-Ethyl-3-(1-pyrrolidinyl)imidazo[1,2-a:3,4-a']diquinolin-15-ium p-Toluenesulfonate; m.p. 268°-275° C., from dimethylformamide/ethyl acetate.

(c) 3-(1-Pyrrolidinyl)imidazo[1,2-a:3,4-a']diquinolin-15-ium p-Toluenesulfonate; m.p. 228°-237° C., from dimethylformamide/ethyl acetate.

(d) 10-Methyl-3-(1-piperidinyl)imidazo[1,2-a:3,4-a']diquinolin-15-ium p-Toluenesulfonate; m.p. 230°-235° C., from methanol/ethyl acetate.

(e) 3-(1-Piperidinyl)imidazo[1,2-a:3,4-a']diquinolin-15-ium p-Toluenesulfonate; m.p. ca 210° C.-220° C., from ethanol/ethyl acetate. 10-(1,1-Dimethylethyl)-3-(1-pyrrolidinyl)imidazo[1,2-a:3,4-a']diquinolin-15-ium Chloride.

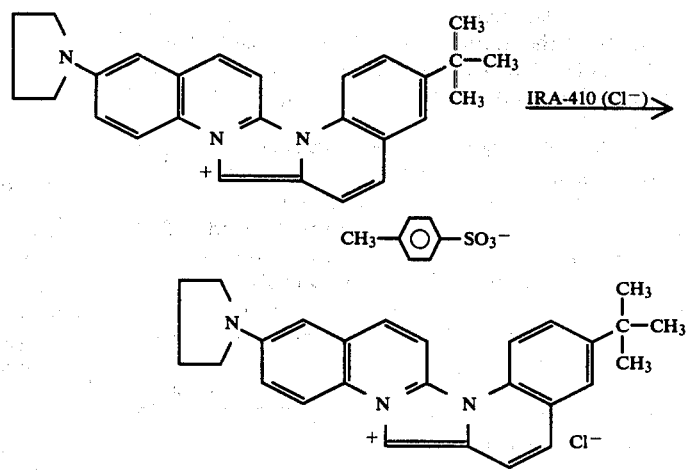

A solution of 150.5 g. of 10-(1,1-dimethylethyl)-3-(1-pyrrolidinyl)imidazo[1,2-a:3,4-a']diquinolin-15-ium p-toluenesulfonate in 6 l. of methanol is passed over a column of 1.7 l. of Amberlite IRA-410 (Cl⁻ form, in methanol) during a period of 6 hours. The eluate is evaporated at reduced pressure to give a residue of 10-(1,1-dimethylethyl)-3-(1-pyrrolidinyl)imidazo[1,2-a:3,4-a']diquinolin-15-ium chloride which is washed with ethyl acetate; m.p. >360° C., after crystallization from 2-propanol/methanol.

In a similar manner, from the corresponding p-toluenesulfonate salt, the following chloride salts are obtained:

(a) 3-(1-Pyrrolidinyl)imidazo[1,2-a:3,4-a']diquinolin-15-ium Chloride; m.p. >360° C., from dimethylformamide/methanol.

(b) 10-Methyl-3-(1-piperidinyl)imidazo[1,2-a:3,4-a']diquinolin-15-ium Chloride; m.p. 260°-320° C., from methanol/ether.

(c) 3-(1-Piperidinyl)imidazo[1,2-a:3,4-a']diquinolin-15-ium Chloride; m.p. 310°–325° C., from methanol.

EXAMPLE 8

10-(1-Methylethyl)-3-(4-methyl-1-piperidinyl)imidazo[1,2-a:3,4-a']diquinolin-15-ium Iodide.

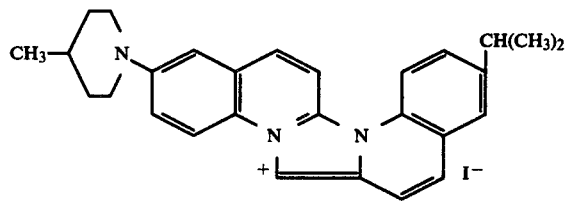

A mixture of 4.7 g. of 3-fluoro-10-(1-methylethyl)imidazo[1,2-a:3,4-a']diquinolin-15-ium iodide, 20 ml. of dimethylformamide and 4.0 ml. of 4-methylpiperidine is stirred and heated at reflux for 1 hour, then evaporated at reduced pressure. The residue is stirred with 75 ml. of ethyl acetate and the resulting precipitate is collected by filtration. The solid is stirred with 150 ml. of 1% aqueous triethylamine hydroiodide, collected by filtration, washed with water and dried. This product is 10-(1-methylethyl-3-(4-methyl-1-piperidinyl)imidazo[1,2-a:3,4-a']diquinolin-15-ium iodide; m.p. 266°–269° C., after crystallization from methanol/acetonitrile.

In a similar manner, by substituting equivalent amounts of the appropriate 3-fluoroimidazo[1,2-a:3,4-a']diquinolin-15-ium iodide and the appropriate amine for the above reactants, the following products are obtained:

(a) 10-(1-Methylethyl)-3-(1-pyrrolidinyl)imidazo[1,2-a:3,4-a']diquinolin-15-ium Iodide; m.p. 327°–335° C. (dec.), from dimethylformamide/methanol.

(b) 10-(1-Methylethyl)-3-(1-piperidinyl)imidazo[1,2-a:3,4-a']diquinolin-15-ium Iodide; m.p. 246°–252° C., from dimethylformamide/ethyl acetate.

(c) 10-Butyl-3-(1-pyrrolidinyl)imidazo[1,2-a:3,4-a']diquinolin-15-ium Iodide; m.p. 162°–170° C. (dec.), from ethanol.

(d) 10-Butyl-3-(1-piperidinyl)imidazo[1,2-a:3,4-a']diquinolin-15-ium Iodide; m.p. 217°–227° C., from aqueous methanol.

EXAMPLE 9

3-(1-Pyrrolidinyl)imidazo[1,2-a:3,4-a']diquinolin-15-ium Iodide.

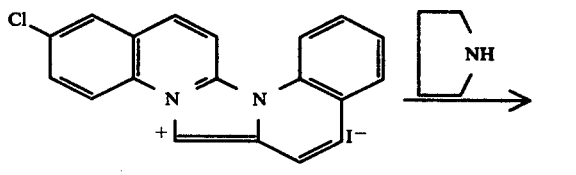

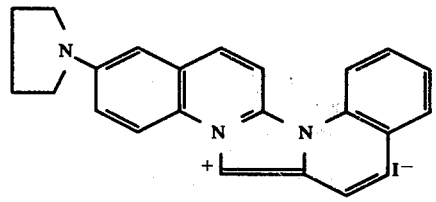

A mixture of 1.0 g. of 3-chloroimidazo[1,2-a:3,4-a']diquinolin-15-ium iodide, 1.0 ml. of pyrrolidine and 5 ml. of N-methyl-2-pyrrolidinone is stirred and heated at reflux for 17 hours, cooled and diluted with 100 ml. of ethyl acetate. The precipitate of 3-(1-pyrrolidinyl)imidazo[1,2-a:3,4-a']diquinolin-15-ium iodide is collected by filtration, stirred with 50 ml. of 1% aqueous triethylamine hydroiodide and recollected; m.p. 312°–320° C. after crystallization from methanol.

EXAMPLE 10

3-(1-Pyrrolidinyl)imidazo[1,2-a:3,4-a']diquinolin-15-ium p-Toluenesulfonate.

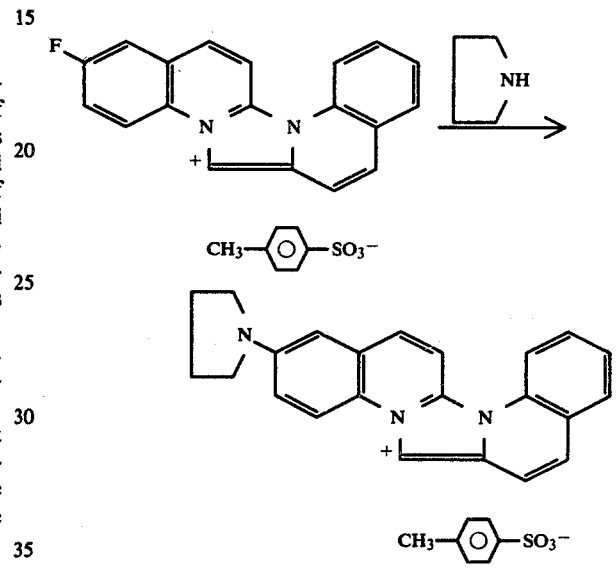

A mixture of 202 g. of 3-fluoroimidazo[1,2-a:3,4-a']diquinolin-15-ium p-toluenesulfonate, 600 ml. of N-methyl-2-pyrrolidinone and 111 ml. of pyrrolidine is heated at reflux (158 C. ) for 45 minutes, then cooled to 0°–5° C. The resulting precipitate of 3-(1-pyrrolidinyl)-imidazo[1,2-a:3,4-a']diquinolin-15-ium p-toluenesulfonate is collected by filtration, washed with ethyl acetate, then with water, and dried; m.p. 228°–237° C.

EXAMPLE 11

10-(1,1-Dimethylethyl)-3-(2,2-dimethylhydrazino)imidazo[1,2-a:3,4-a']diquinolin-15-ium Iodide

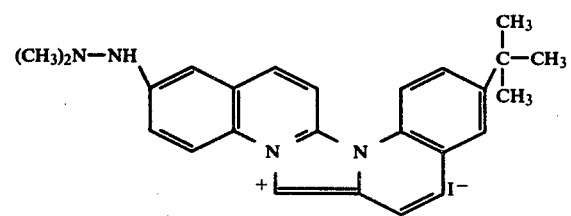

A mixture of 1.46 g. of 10-(1,1-dimethylethyl)-3-fluoroimidazo-[1,2-a:3,4-a']diquinolin-15-ium iodide, 1.64 ml. of 1,1-dimethylhydrazine and 25 ml. of N-methyl-2-pyrrolidinone is heated at reflux for 15 hours, then cooled and diluted with 300 ml. of ethyl acetate. The precipitate is collected and stirred with 1% aqueous triethylamine hydroiodide. The solid is collected, washed with water and dissolved in 150 ml. of hot methanol. The methanol solution is treated with activated charcoal, filtered, evaporated to a volume of about 25 ml. and cooled. The resulting precipitate of 10-(1,1-dimethylethyl)-3-(2,2-dimethylhydrazino)imidazo[1,2-a:3,4-a']diquinolin-15-ium iodide is collected by filtration, washed with cold methanol and dried; m.p. 347°–350° C., after two crystallizations from 2-propanol/ethanol.

EXAMPLE 12

10-(4-Morpholinyl)imidazo[1,2-a:3,4-a']diquinolin-15-ium Iodide.

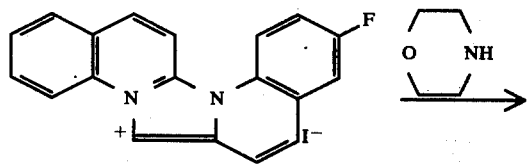

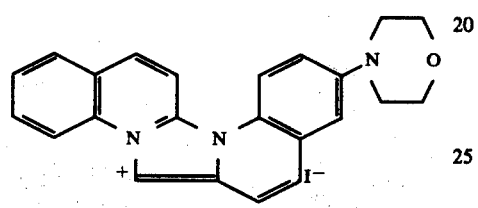

A mixture of 1.04 g. of 10-fluoroimidazo[1,2-a:3,4-a']diquinolin-15-ium iodide, 3.0 ml. of morpholine and 40 ml. of dimethylformamide is heated at gentle reflux for 40 hours, treated with 1.5 g. of sodium iodide and evaporated at reduced pressure to give 10-(4-morpholinyl)imidazo[1,2-a:3,4-a']diquinolin-15-ium iodide; m.p. >300° C. after two crystallizations from aqueous methanol.

In a similar manner, by substituting an equivalent amount of piperidine for the morpholine in the above example, the following product is obtained:

(a) 10-(1-Piperidinyl)imidazo[1,2-a:3,4-a']diquinolin-15-ium Iodide; m.p. 270°–300° C. (dec.), from methanol.

EXAMPLE 13

10-(N-Methylbutylamino)imidazo[1,2-a:3,4-a']diquinolin-15-ium Iodide.

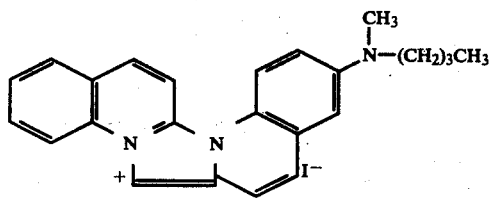

A mixture of 1.87 g. of 10-fluoroimidazo[1,2-a:3,4-a']diquinolin-15-ium iodide, 2.0 ml. of N-methylbutylamine and 10 ml. of dimethyl sulfoxide is heated at gentle reflux for 8 hours, cooled and diluted with 125 ml. of ether. The supernatant solvent is decanted and the solid is crystallized from aqueous methanol containing 1.5 g. of dissolved sodium iodide to give 10-(methylbutylamino)imidazo[1,2-a:3,4-a']diquinolin-15-ium iodide; m.p. 236°–240° C., after crystallizations from 95% ethanol (with a charcoal treatment) and from methanol/ethyl acetate.

In a similar manner, by substituting equivalent amounts of the appropriate 10-fluoroimidazo[1,2-a:3,4-a']diquinolin-15-ium iodide and the appropriate amine for the above reactants, the following products are obtained:

(a) 10-Cyclohexylaminoimidazo[1,2-a:3,4-a']diquinolin-15-ium Iodide, Hydroiodide; m.p. 257°–260° C., from methanolic hydrogen iodide.

(b) 3-Methyl-10-(4-morpholinyl)imidazo[1,2-a:3,4-a']diquinolin-15-ium Iodide; m.p. 310° C., from methanol.

(c) 10-Hexylaminoimidazo[1,2-a:3,4-a']diquinolin-15-ium Iodide; m.p. 200°–205° C., from 2-propanol.

(d) 3-Methyl-10-(N-methylbutylamino)imidazo[1,2-a:3,4-a']diquinolin-15-ium Iodide; m.p. 230°–233° C., from methanol.

EXAMPLE 14

10-Dimethylaminoimidazo[1,2-a:3,4-a']diquinolin-15-ium Iodide.

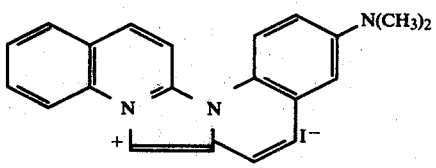

A mixture of 3.11 g. of 10-fluoroimidazo[1,2-a:3,4-a]diquinolin-15-ium iodide, 2.74 g. of diethylamine and 31 ml. of N-methyl-2-pyrrolidinone is stirred and heated in a pressure vessel at 190° C. for 12 hours, then evaporated at reduced pressure. The residue is stirred with 15 ml. of benzene and 150 ml. of ethyl acetate and the resulting precipitate of 10-dimethylaminoimidazo[1,2-a:3,4-a']diquinolin-15-ium iodide is collected by filtration, washed with ethyl acetate and dried; m.p. 253°–270° C., after two crystallizations from methanol.

EXAMPLE 15

2-Methyl-10-(4-morpholinyl)imidazo[1,2-a:3,4-a']diquinolin-15-ium Iodide.

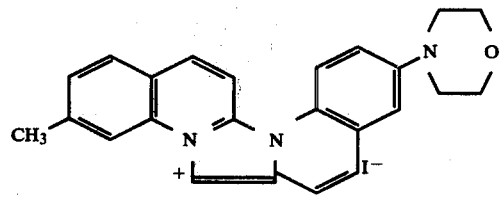

A mixture of 1.0 g. of 10-fluoro-2-methyldiquinolin-15-ium iodide, 50 ml. of morpholine and 50 ml. of morpholine and 50 ml. of ethylene glycol is heated at gentle reflux for 5 days, then evaporated at reduced pressure. The residue is triturated with 40 ml. of ethanol and the resulting precipitate of 2-methyl-10-(4-morpholinyl)imidazo[1,2-a:3,4-a']diquinolin-15-ium iodide is collected by filtration; m.p. 271°–292° C. (dec.), after two crystallizations from methanol.

EXAMPLE 16

10-(1-Pyrrolidinyl)imidazo[1,2-a:3,4-a']diquinolin-15-ium Iodide.

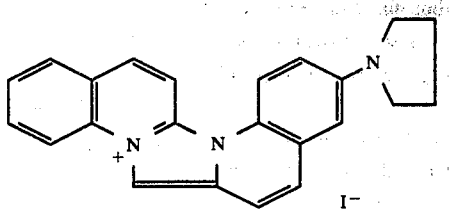

A mixture of 4.14 g. of 10-fluoroimidazo[1,2-a:3,4-a']diquinolin-15-ium iodide, 3.6 g. of pyrrolidine and 100 ml. of methanol is stirred and heated in a pressure vessel at 190° C. for 24 hours, then cooled and evaporated at reduced pressure. The resulting precipitate of 10-(1-pyrrolidinyl)imidazo[1,2-a:3,4-a']diquinolin-15-ium iodide is collected and washed with cold methanol; m.p. 350°-355° C., after crystallization from dimethylformamide.

In a similar manner, by substituting equivalent amounts of the appropriate 10-fluoroimidazo[1,2-a:3,4-a']diquinolin-15-ium iodide and the appropriate amine for the above reactants, the following products are obtained:

(a) 10-Methylaminoimidazo[1,2-a:3,4-a']diquinolin-15-ium Iodide; m.p. 322°-325° C., from dimethylformamide.

(b) 10-Ethylaminoimidazo[1,2-a:3,4-a']diquinolin-15-ium Iodide; m.p. 285°-290° C., from dimethylformamide/2-propanol.

(c) 10-(N-Methylethylamino)imidazo[1,2-a:3,4-a]diquinolin-15-ium Iodide; m.p. 283°-286° C., from dimethylformamide/methanol.

(d) 2-Methyl-10-dimethylaminoimidazo[1,2-a:3,4-a']diquinolin-15-ium Iodide; m.p. 272°-310° C. (dec.), from methanol/ethylene glycol.

(e) 10-(N,2-Dimethylpropylamino)imidazo[1,2-a:3,4']diquinolin-15-ium Iodide; m.p. 270°-275° C., from dimethylformamide/2-propanol.

(f) 10-Dimethylamino)-3-methylimidazo[1,2-a:3,4-a']diquinolin-15-ium Iodide; m.p. 360° C., from dimethylformamide, obtained with ½ formula weight of dimethylformamide of crystallization.

(g) 2-Methyl-10-(1-pyrrolidinyl)imidazo[1,2-a:3,4-a]diquinolin-15-ium Iodide; m.p. 275°-308° C. (dec.), from methanol.

(h) 10-(N-Methylbenzylamino)imidazo[1,2-a:3,4-a']diquinolin-15-ium Iodide; m.p. 318°-319° C., from dimethylformamide/methanol.

(i) 10-Benzylaminoimidazo[1,2-a:3,4-a']diquinolin-15-ium Iodide; m.p. 190°-195° C., from dimethylformamide/methanol.

(j) 10-(2-Ethoxyethylamino)imidazo[1,2-a:3,4-a']diquinolin-15-ium Iodide; m.p. 203°-210° C., from dimethylformamide/2-propanol.

(k) 10-Dimethylamino-3-ethylimidazo[1,2-a:3,4-a']diquinolin-15-ium Iodide; m.p. 318°-320° C., from dimethylformamide/methanol.

(l) 10-(3-Methoxypropylamino)imidazo[1,2-a:3,4-a']diquinolin-15-ium Iodide; m.p. 179°-182° C., from methanol.

(m) 3-Methyl-10-(1-piperidinyl)imidazo[1,2-a']diquinolin-15-ium Iodide; m.p. 205°-295° C., from methanol.

(n) 10-(2-Methyl-1-pyrrolidinyl)imidazo[1,2-a:3,4-a']diquinolin-15-ium Iodide; m.p. 303°-307° C., from methanol.

(o) 10-(3-Methyl-1-pyrrolidinyl)imidazo[1,2-a:3,4-a']diquinolin-15-ium Iodide; m.p. 325°-330° C., from methanol.

(p) 3-(1-Methylethyl)-10-(1-pyrrolidinyl)imidazo[1,2-a:3,4-a']diquinolin-15-ium Iodide; m.p. 312°-314° C., from methanol.

(q) 10-Dimethylamino-3-(1,1-dimethylethyl)imidazo[1,2-a:3,4-a']diquinolin-15-ium Iodide; m.p. >360° C., from methanol.

(r) 10-Dimethyl-3-(1-methylethyl)imidazo[1,2-a:3,4-a']diquinolin-15-ium Iodide; m.p. 310°-316° C. (dec.), from methanol/ethyl acetate.

(s) 3-Butyl-10-(dimethylamino)imidazo[1,2-a:3,4-a']diquinolin-15-ium Iodide; m.p. 272°-285° C. (dec.), from methanol/ether.

(t) 3-Cyclohexyl-10-dimethylaminoimidazo[1,2-a:3,4-a']diquinolin-15-ium Iodide; m.p. 220°-240° C. (dec.), from methanol.

(u) 3-Cyclohexyl-10-(1-pyrrolidinyl)imidazo[1,2-a:3,4-a']diquinolin-15-ium Iodide; m.p. 282°-297° C. (dec.), from N-methyl-2-pyrrolidinone/ether.

EXAMPLE 17

3-Methyl-10-(1-pyrrolidinyl)imidazo[1,2-a:3,4-a']diquinolin-15-ium p-Toluenesulfonate.

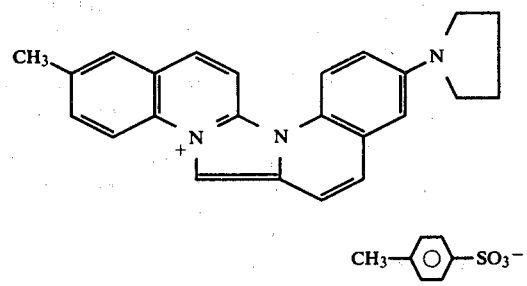

A mixture of 14.4 g. of 3-methyl-10-fluoroimidazo[1,2-a:2,3-a']diquinolin-15-ium p-toluenesulfonate, 300 ml. of methanol and 15 ml. of pyrrolidine is stirred and heated in a pressure vessel at 190° C. for 24 hours, then evaporated at 90°-100° C. in a current of air. The residue is dissolved in methanol and the solution is evaporated at reduced pressure to give 3-methyl-10-(1-pyrrolidinyl)imidazo[1,2-a:3,4-a']diquinolin-15-ium p-toluenesulfonate; m.p. 233°-248° C., after crystallization from methanol/ethyl acetate.

The above p-toluenesulfonate salt is dissolved in 250 ml. of methanol, and the solution is passed over a column of 95 ml. of IRA-410 resin (OH⁻ form, in methanol) over a period of 4.5 hours. The column is washed with methanol until a total eluate of 324 ml. is collected, containing the hydroxide salt of the 3-methyl-10-(1-pyrrolidinyl)imidazo[1,2-a:3,4-a']diquinolin-15-ium cation. Portions of this solution are used to prepare the following salts by reaction with an equivalent of the designated acid in methanol, followed by evaporation and crystallization:

(a) 3-Hydroxy-2-naphthoate; m.p. 283°-302° C. (dec.), from methanol/ether.

(b) Salicylate; m.p. 292°–302° C. (dec.), from methanol/acetonitrile.
(c) 5-Acetyl-8-hydroxyquinoline Salt; m.p. 249°–250° C. (dec.), from methanol/ether.
(d) Chloride; m.p. 315°–330° C. (dec.), from methanol/acetonitrile.
(e) Bromide; m.p. 300°–308° C. (dec.), from ethanol
(f) Lactate; m.p. 135°–140° C. (dec.), from acetonitrile,
(g) Benzoate; m.p. 265°–275° C. (dec.), from ethanol/ethyl acetate.

EXAMPLE 18

10-Dimethylamino-3-ethylimidazo[1,2-a:3,4-a']diquinolin-15-ium p-Toluenesulfonate

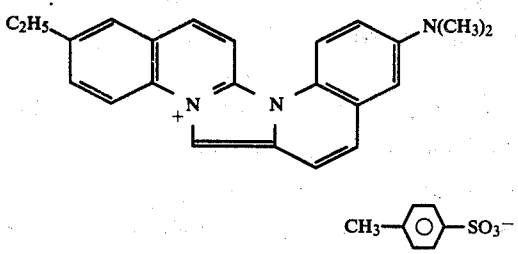

A stirred mixture of 5.5 g. of 10-dimethylamino-3-ethylimidazo[1,2-a:3,4-a']diquinolin-15-ium iodide and 80 ml. of dimethylformamide is heated to 50° C. and nitrogen is bubbled into the suspension. Methyl p-toluenesulfonate (4.2 g.) is added, the mixture is stirred at 50° C. with continuous nitrogen flow for 1.5 hours, then diluted with 200 ml. of ethyl acetate and cooled to 5° C. The resulting precipitate of 10-dimethylamino-3-ethylimidazo[1,2-a:3,4-a']diquinolin-15-ium p-toluenesulfonate is collected by filtration and washed with ethyl acetate; m.p. 227°–230° C., after crystallization from methanol/acetonitrile.

In a similar manner, by substituting an equivalent amount of 3-butyl-10-(1-piperidinyl)imidazo[1,2-a:3,4-a']diquinolin-15-ium iodide for the 10-dimethylamino-3-ethylimidazo[1,2-a:3,4-a']diquinolin-15-ium iodide in the above example, the following product is obtained:
(a)  3-Butyl-10-(1-piperidinyl)imidazo[1,2-a:3,4-a']diquinolin-15-ium p-Toluenesulfonate; m.p. ca 160° C.–170° C.

EXAMPLE 19

10-(1-Azetidinyl)-3-ethylimidazo[1,2-a:3,4-a']diquinolin-15-ium Iodide.

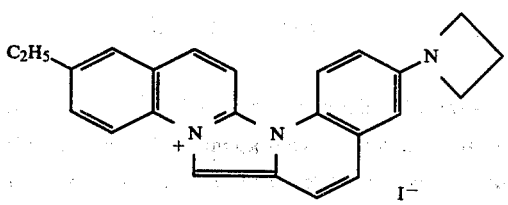

A stirred mixture of 2.21 g. of 3-ethyl-10-fluoroimidazo[1,2-a:3,4-a']diquinolin-15-ium iodide, 15 ml. of dimethylformamide and 1.0 ml. of azetidine is heated at 72° C. for 3 days in a pressure vessel, then cooled, treated with 0.5 ml. of azetidine and allowed to stand at 20°–25° C. for 7 days, with occasional agitation. The resulting precipitate of 10-(1-azetidinyl)-3-ethylimidazo[1,2-a:3,4-a']diquinolin-15-ium iodide is collected by filtration, washed with water and dried; m.p. 270°–275° C., after crystallization from methanol.

EXAMPLE 20

3-Butyl-10-(1-piperidinyl)imidazo[1,2-a:3,4-a']diquinolin-15-ium Iodide.

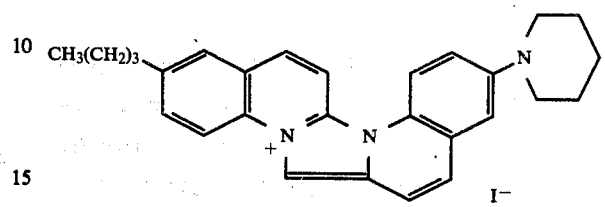

A mixture of 4.7 g. of 3-butyl-10-fluoroimidazo[1,2-a:3,4-a']diquinolin-15-ium iodide, 5.0 ml. of piperidine and 50 ml. of N-methyl-2-pyrrolidinone is heated at reflux for 16 hours, then cooled and diluted with 400 ml. of ether. The resulting precipitate of 3-butyl-10-(1-piperidinyl)imidazo[1,2-a:3,4-a']diquinolin-15-ium iodide is collected by filtration; m.p. 266°–267° C. (dec.), after crystallization from ethanol.

In a similar manner, by substituting equivalent amounts of the appropriate 10-fluoroimidazo[1,2-a:3,4-a']diquinolin-15-ium iodide and the appropriate amine for the above reactants, the following products are obtained:
(a)  10-(2-Methoxyethylamino)-3-methylimidazo[1,2-a:3,4-a']diquinolin-15-ium Iodide; m.p. 271°–273° C., from dimethylformamide/2-propanol.
(b)  2-Methyl-10-(N-methylbutylamino)imidazo[1,2-a:3,4-a']diquinolin-15-ium Iodide; m.p. 220°–227° C. (dec.), from methanol.
(c)  10-(2-Methoxyethylamino)imidazo[1,2-a:3,4-a']diquinolin-15-ium Iodide, Hydroiodide; m.p. 205°–212° C., from aqueous methanolic hydrogen iodide.
(d)  10-(2-Methoxyethylamino)-2-methylimidazo[1,2-a:3,4-a']diquinolin-15-ium Iodide; m.p. 175°–218° C., from methanol.
(e)  3-Ethyl-10-(N-methylbutylamino)imidazo[1,2-a:3,4-a']diquinolin-15-ium Iodide; m.p. 254°–261° C., from 2-propanol.
(f)  3-Ethyl-10-(4-morpholinyl)imidazo[1,2-a:3,4-a']diquinolin-15-ium Iodide; m.p. 266°–274° C. (dec.), from dimethylformamide/2-propanol.
(g)  3-Methyl-10-(1-pyrrolidinyl)imidazo[1,2-a:3,4-a']diquinolin-15-ium Iodide; m.p. 318°–328° C., from dimethylformamide.
(h)  3-Ethyl-10-(1-pyrrolidinyl)imidazo[1,2-a:3,4-a']diquinolin-15-ium Iodide; m.p. 331°–337° C., from dimethylformamide.
(i)  3-Ethyl-10-(1-piperidinyl)imidazo[1,2-a:3,4-a']diquinolin-15-ium Iodide; m.p. 325°–330° C., from dimethylformamide/2-propanol.
(j)  10-(2-Phenylethylamino)imidazo[1,2-a:3,4-a']diquinolin-15-ium Iodide; m.p. 252°–259° C., from dimethylformamide/methanol.
(k) 3-Ethyl-10-(hexahydro-1H-azepin-1-yl)imidazo[1,2-a:3,4-a']diquinolin-15-ium Iodide; m.p. 331°–335° C., from methanol.
(l)  10-(Hexahydro-1H-azepin-1-yl)imidazo[1,2-a:3,4-a']diquinolin-15-ium Iodide; m.p. 318°–323° C., from methanol.

(m) 10-(4-Methyl-1-piperidinyl)imidazo[1,2-a:3,4-a']diquinolin-15-ium Iodide; m.p. 233°-275° C. (dec.), from N-methyl-2-pyrrolidinone/ether.

(n) 3-Butyl-10-(1-pyrrolidinyl)imidazo[1,2-a:3,4-a']diquinolin-15-ium Iodide; m.p. 265°-281° C. (dec.), from methanol.

(o) 3-(1,1-Dimethylethyl)-10-(1-pyrrolidinyl)imidazo[1,2-a:3,4-a']diquinolin-15-ium Iodide; m.p. 350°-354° C., from N-methyl-2-pyrrolidinone/ether.

(p) 3-(1-Methylethyl)-10-(1-piperidinyl)imidazo[1,2-a:3,4-a']diquinolin-15-ium Iodide; m.p. 295°-300° C., from methanol.

(q) 3-(1,1-Dimethylethyl)-10-(1-piperidinyl)imidazo[1,2-a:3,4-a']diquinolin-15-ium Iodide; m.p. 354°-358° C., from ethanol.

EXAMPLE 21

3-Butyl-10-(1-piperindinyl)imidazo[1,2-a:3,4-a']diquinolin-15-ium Chloride

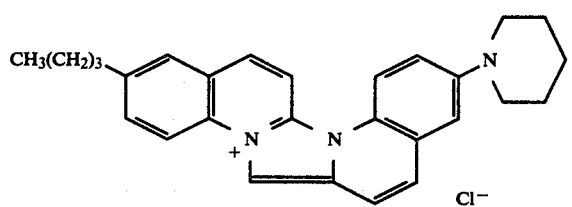

A solution of 69.0 g. of 3-butyl-10-(1-piperidinyl)imidazo[1,2-a:3,4-a']diquinolin-15-ium p-toluenesulfonate in 1.2 l. of methanol is passed through a column of 1.0 l. of IRA-410 resin (Cl⁻ form, in methanol) over a period of 3 hours. The eluate is concentrated to a volume of 100 ml. and the solution is added dropwise, with stirring, to 1.0 l. of diethyl ether. The resulting precipitate of 3-butyl-10-(1-piperindinyl)imidazo[1,2-a:3,4-a']diquinolin-15-ium chloride is collected by filtration, washed with ether and dried; m.p. 209°-211° C. (dec.).

EXAMPLE 22

3,10-Di-(1-pyrrolidinyl)imidazo[1,2-a:3,4-a']diquinolin-15-ium Iodide.

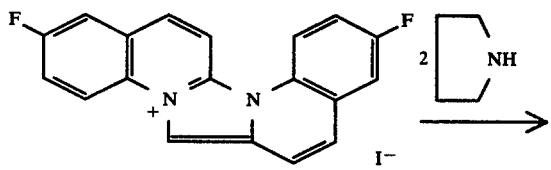

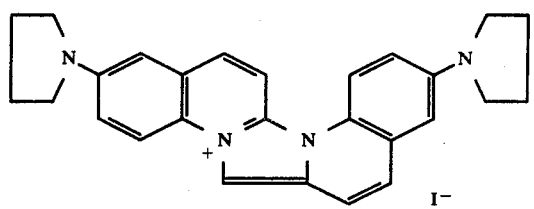

A mixture of 4.41 g. of 3,10-difluoroimidazo[1,2-a:3,4-a']diquinolin-15-ium iodide, 9.0 ml. of pyrrolidine and 130 ml. of N-methyl-2-pyrrolidinone is stirred and heated at 130°-160° C. for 4.5 hours, then cooled. The resulting precipitate is collected, washed with methanol and stirred with 100 ml. of 2% aqueous triethylamine hydroiodide for 1 hour. The resulting precipitate of 3,10-di-(1-pyrrolidinyl)imidazo[1,2-a:3,4-a']diquinolin-15-ium iodide is collected by filtration, washed with water and dried; m.p. 345° C. (dec.), after crystallization from dimethylformamide/-2-propanol.

In a similar manner, by substituting an equivalent amount of the appropriate amine for the pyrrolidine in the above example, the following products are obtained:

(a) 3,10-Di-(1-piperidinyl)imidazo[1,2-a:3,4-a']diquinolin-15-ium Iodide; m.p. 195°-225° C. (dec.), from dimethylformamide/2-propanol.

(b) 3,10-Di-(4-methyl-1-piperidinyl)imidazo[1,2-a:3,4-a']diquinolin-15-ium Iodide; m.p. ca 270° C.-290° C., from N-methyl-2-pyrrolidinone/acetonitrile.

EXAMPLE 23

3,10-Di-(dimethylamino)imidazo[1,2-a:3,4-a']diquinolin-15-ium Iodide.

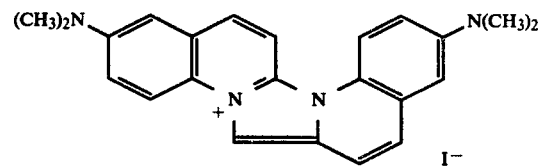

A stirred mixture of 4.41 g. of 3,10-difluoroimidazo[1,2-a:3,4-a']diquinolin-15-ium iodide, 6.0 g. of dimethylamine and 500 ml. of methanol is heated in a pressure vessel at 190° C. for 48 hours, then cooled. The precipitate is collected and stirred with 150 ml. of 0.5% aqueous triethylamine hydroiodide for 1 hour. The resulting solid 3,10-di-(dimethylamino)imidazo[1,2-a:3,4-a']diquinolin-15-ium iodide is collected by filtration, washed with water and dried; m.p. 360° C. (dec.).

EXAMPLE 24

3,10-Di-(4-methyl-1-piperidinyl)imidazo[1,2-a:3,4-a']diquinolin-15-ium p-Toluenesulfonate.

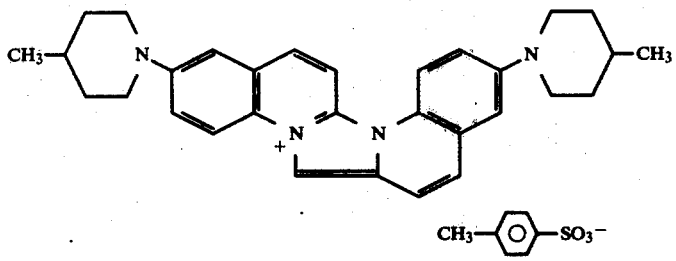

A mixture of 5.2 g. of 3,10-di-(4-methyl-1-piperidinyl)imidazo[1,2-a:3,4-a']diquinolin-15-ium iodide, 100 ml. of dimethylformamide and 3.0 g. of methyl p-toluenesulfonate is stirred and heated at 50°–55° C. for 1 hour while nitrogen is bubbled through the mixture. The mixture is cooled, diluted with 400 ml. of ethyl acetate and the resulting precipitate of 3,10-di-(4-methyl-1-piperidinyl)imidazo[1,2-a:3,4-a']diquinolin-15-ium p-toluenesulfonate is collected by filtration; m.p. 266°–267° C., after crystallization from methanol/acetonitrile/ethyl acetate.

In a similar manner, from the corresponding iodide salt, the following p-toluenesulfonate salts are obtained:

(a) 3,10-Di-(1-pyrrolidinyl)imidazo[1,2-a:3,4-a']diquinolin-15-ium p-Toluenesulfonate; m.p. 208°–220° C. (dec.), from acetonitrile.
(b) 3,10-Di-(1-piperidinyl)imidazo[1,2-a:3,4-a']diquinolin-15-ium p-Toluenesulfonate; m.p. 250°–260° C. (dec.), from ethanol.

EXAMPLE 25

3,10-Di-(4-methyl-1-piperidinyl)imidazo[1,2-a:3,4-a']diquinolin-15-ium Chloride.

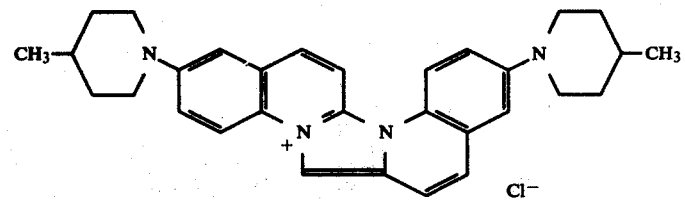

A solution of 4.8 g. of 3,10-di-(4-methyl-1-piperidinyl)imidazo[1,2-a:3,4-a']diquinolin-15-ium p-toluenesulfonate in 500 ml. of methanol is passed over a column of 95 ml. of IRA-410 resin (Cl⁻ form, in methanol) over a period of 3 hours. The eluate is evaporated at reduced pressure to give a residue of 3,10-di-(4-methyl-1-piperidinyl)imidazo[1,2-a:3,4-a']diquinolin-15-ium chloride; m.p. 277°–300° C. (dec.), after crystallization from acetonitrile.

EXAMPLE 26

10-Ethyl-3-(1-pyrrolidinyl)imidazo[1,2-a:3,4-a']diquinolin-15-ium chloride

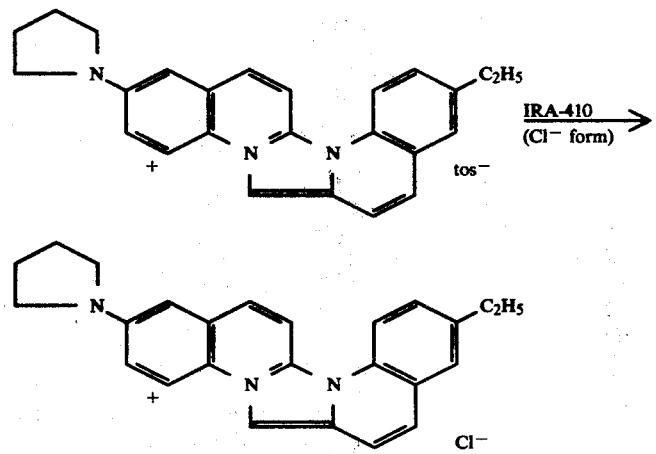

A solution of 242.4 g of 10-ethyl-3-(1-pyrrolidinyl)imidazo[1,2-a:3,4-a']diquinolin-15-ium p-toluenesulfonate in 3 l of methanol is passed over a column of 1.7 l of Amberlite IRA-410 (Cl⁻ form, in methanol) during a period of 4.5 hr. The eluate is evaporated at reduced pressure to give a residue of 10-ethyl-3-(1-pyrrolidinyl)imidazo[1,2-a:3,4-a']diquinolin-15-ium chloride which

EXAMPLE 27

3-(1-Pyrrolidinyl)imidazo[1,2-a: 3,4-a']diquinolin-15-ium chloride

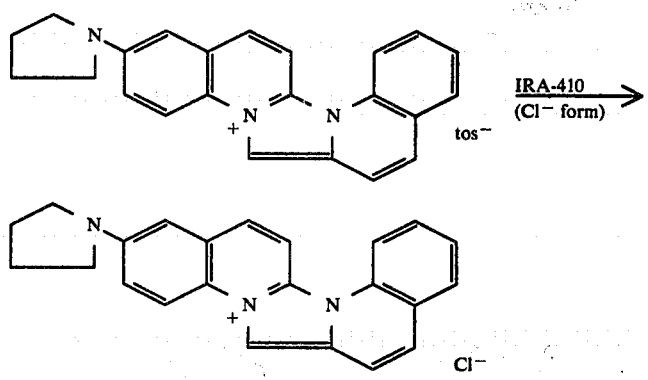

A solution of 202.9 g of 3-(1-pyrrolidinyl)imidazo[1,2-a: 3,4-a']diquinolin-15-ium p-toluenesulfonate in 4.5 l of methanol is passed over a column of 1.7 l of Amberlite IRA-410 (Cl⁻form, in methanol) during a period of 4 hr. The eluate is evaporated at reduced pressure to give a residue of 3-(1-pyrrolidinyl)imidazo[1,2-a: 3,4-a']diquinolin-15-ium chloride which is washed with ethyl acetate; mp >360° C., from ethanol-ethyl acetate.

EXAMPLE 28

6-(1,1-Dimethylethyl)quinoline

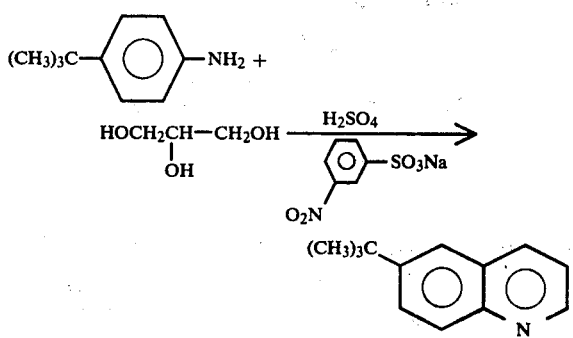

4-(1,1-Dimethylethyl)aniline (185 g.) is added dropwise, with stirring, to 500 ml. of 75% sulfuric acid, followed by 376 g. of sodium 3-nitrobenzenesulfonate in one portion, then 212 g. of glycerol over a 10 minute period. The mixture is stirred for 10 minutes, heated slowly to reflux temperature over a 2.5 hour period, then stirred and heated at reflux for 9 hours. The mixture is cooled, diluted with 400 ml. of ice water, basified with 855 ml. of 50% aqueous sodium hydroxide and warmed to 70° C. The supernatant solution is decanted and extracted with toluene. The toluene extract is in turn extracted with three 800 ml. portions of 2 N hydrochloric acid. The combined acid extract is basified with excess 50% aqueous sodium hydroxide and extracted with toluene. The toluene extract is evaporated at reduced pressure to give a residue of 6-(1,1-dimethylethyl)quinoline which is purified by distillation; b.p. 90°-94° C./0.18 mm.

By substituting an equivalent amount of the appropriately substituted aniline for the 4-(1,1-dimethylethyl)aniline in the above example, the following quinolines are obtained.

(a) 6-Cyclohexylquinoline. m.p. 48°-48.5° C., after crystallization from hexane.

(b) 6-Fluoroquinoline. b.p. 93°-94° C./9 mm.

EXAMPLE 29

6-Butylquinaldine

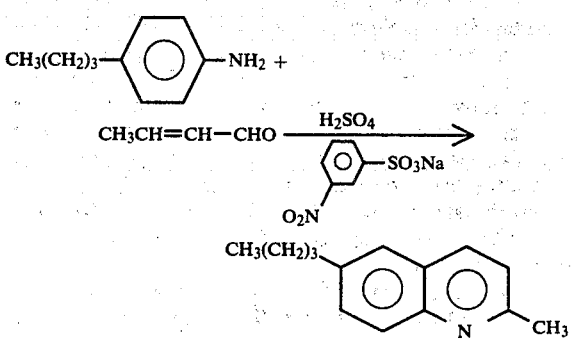

A stirred mixture of 200 ml. of water, 269 g. of concentrated sulfuric acid and 136 g. of sodium 3-nitrobenzenesulfonate at 75° C. is treated dropwise with 149 g. of 4-butylaniline. The mixture is heated to 105° C. and 117 g. of crotonaldehyde is added dropwise, with stirring, at such a rate that the temperature is maintained at 105° C. The mixture is then heated at 114° C. for 30 minutes, cooled to 80° C. and poured onto chipped ice. The mixture is basified with 50% aqueous sodium hydroxide and steam distilled. The distillate is extracted with dichloromethane. The extract is evaporated at reduced pressure leaving a residue of crude 6-butylquinaldine which is distilled at reduced pressure; b.p. 104°-106° C./0.5 mm. This product is further purified by dissolving it in 600 ml. of ether and treating the solution with 23 ml. of acetic anhydride. After standing for 20 minutes, the solution is extracted with 500 ml. of 10% hydrochloric acid. The acid extract is basified with 50% aqueous sodium hydroxide and extracted with ether. The ether extract is washed with water, dried and evaporated to give a residue of purified 6-butylquinaldine.

In a similar manner, by substituting an equivalent amount of the appropriately substituted aniline for the 4-butylaniline in the above example, the following quinaldines are obtained:

(a) 6-(1,1-Dimethylethyl)quinaldine.
(b) 6-Propylquinaldine.
(c) 6-(1-Methylethyl)quinaldine. b.p. 98° C./0.12 mm.

EXAMPLE 30

3-Fluoroimidazo[1,2-a: 3,4-a']diquinolin-15-ium Iodide

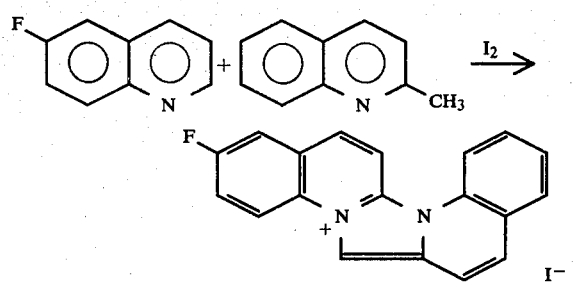

A mixture of 294 g. of 6-fluoroquinoline, 74.6 g. of quinaldine, 1.7 l. of chlorobenzene and 254 g. of iodine is stirred for 2 hours at 20°-25° C., then stirred and heated at 100° C. for 4 days. About 1 l. of solvent is removed by evaporation at reduced pressure and the residue is cooled to 0°-5° C. The precipitate is collected, washed with cold chlorobenzene, dried and pulverized. The finely divided solid is suspended with stirring and cooling in 500 ml. of methanol and 55 ml. of hydrazine is added to destroy excess iodine. The resulting solid 3-fluoroimidazo[1,2-a:3,4-a']diquinolin-15-ium iodide is collected by filtration, washed with cold methanol and dried; m.p. 310°-316° C.

In a similar manner, from the appropriate quinoline and quinaldine, the following products are obtained:
(a) 3-Chloroimidazo[1,2-a:3,4-a']diquinolin-15-ium Iodide; m.p. 344°-346° C.
(b) 3-Fluoro-10-methylimidazo[1,2-a:3,4-a']diquinolin-15-ium Iodide; m.p. 341°-345° C. from methanol.
(c) 10-Ethyl-3-fluoroimidazo[1,2-a:3,4-a']diquinolin-15-ium Iodide; m.p. 314°-320° C., from methanol.
(d) 3-Fluoro-10-propylimidazo[1,2-a:3,4-a']diquinolin-15-ium Iodide m.p. 290°-291° C., from aqueous methanol.

EXAMPLE 31

3-Fluoro-10-methylimidazo[1,2-a:3,4-a']diquinolin-15-ium Chloride

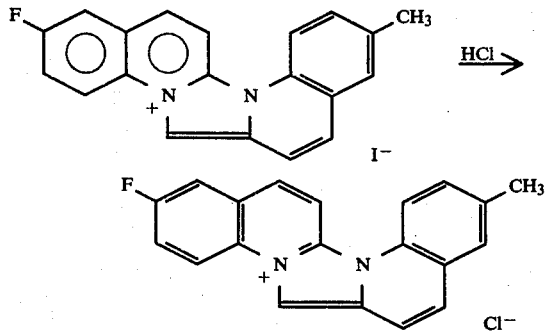

A hot solution of 88 g. of 3-fluoro-10-methylimidazo[1,2-a:3,4-a']diquinolin-15-ium iodide in 6.4 l. of 6 N hydrochloric acid is cooled and the resulting precipitate of 3-fluoro-10-methylimidazo[1,2-a:3,4-a']diquinolin-15-ium chloride is collected by filtration, washed with 0.4 N hydrochloric acid, then with acetone, and dried; m.p. 345°-350° C. (dec.).

EXAMPLE 32

3-Fluoro-10-(1-methylethyl)imidazo[1,2-a:3,4-a']diquinolin-15-ium Iodide

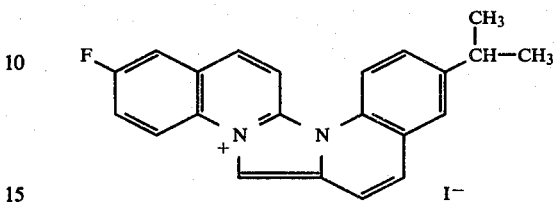

A solution of 88.3 g. of 6-fluoroquinoline, 27.8 g. of 6-(1-methylethyl)quinaldine and 76.2 g. of iodine in 100 ml. of toluene is heated at 95°-100° C. for 5 days, cooled and diluted with 350 ml. of ethyl acetate. The precipitate is collected, pulverized, suspended in 500 ml. of aqueous methanol and recovered by filtration. The solid is suspended in 400 ml. of cold methanol, stirred with 6 ml. of hydrazine and the solid 3-fluoro-10-(1-methylethyl)imidazo[1,2-a:3,4-a']diquinolin-15-ium iodide is collected by filtration; m.p. 305°-307° C., after crystallization from methanol.

In a similar manner, from the appropriate quinoline and quinaldine, the following products are obtained:
(a) 3-Fluoro-10-(1,1-dimethylethyl)imidazo[1,2-a:3,4-a']diquinolin-15-ium Iodide; m.p. 352°-355° C., from methanol.
(b) 10-Butyl-3-fluoroimidazo[1,2-a:3,4-a']diquinolin-15-ium Iodide; m.p. 245°-256° C., from aqueous methanol.

EXAMPLE 33

10-fluoroimidazo[1,2-a:3,4-a']diquinolin-15-ium Iodide

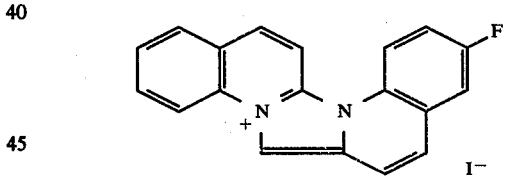

A mixture of 614 g. of quinoline, 192 g. of 6-fluoroquinaldine [J. Org. Chem. 42, 911 (1977)], 2.0 l. of chlorobenzene and 602 g. of iodine is stirred at 25°-30° C. for 2 hours, then heated at 95°-100° C. for 90 hours. The mixture is cooled and the precipitate is collected, washed with cold chlorobenzene and suspended in 1.5 l. of methanol. The methanol suspension is stirred with 150 ml. of hydrazine hydrate and the resulting solid 10-fluoroimidazo[1,2-a:3,4-a']diquinolin-15-ium iodide is collected by filtration; m.p. 330°-334° C., after crystallization from methanol.

In a similar manner, from the appropriate quinoline and quinaldine, the following products are obtained:
(a) 3-Ethyl-10-fluoroimidazo[1,2-a:3,4-a']diquinolin-15-ium Iodide; m.p. 301°-304° C., from methanol.
(b) 10-Fluoro-3-(1-methylethyl)imidazo[1.2-a:3,4-a']diquinolin-15-ium Iodide; m.p. 330°-335° C. (dec.), from methanol.
(c) 10-Fluoro-2-methylimidazo[1,2-a:3,4-a']diquinolin-15-ium Iodide; m.p. 362°-365° C. (dec.), from methanol.

EXAMPLE 34

10-Fluoro-3-methylimidazo[1,2-a:3,4-a']diquinolin-15-ium Iodide

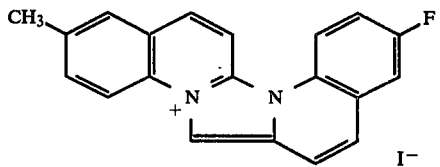

A mixture of 24.2 g. of 6-fluoroquinaldine, 86 g. of 6-methylquinoline, 100 ml. of chlorobenzene and 76 g. of iodine is stirred at 20°-25° C. until solution is obtained, then heated at 95°-100° C. for 3 days. The mixture is cooled and the precipitate of 10-fluoro-3-methylimidazo[1,2-a:3,4-a']diquinolin-15-ium iodide is collected by filtration, washed with chlorobenzene, then with methanol and dried; m.p. 360° C. after crystallization from dimethylformamide.

EXAMPLE 35

3-Butyl-10-fluoroimidazo[1,2-a:3,4-a']diquinolin-15-ium Iodide.

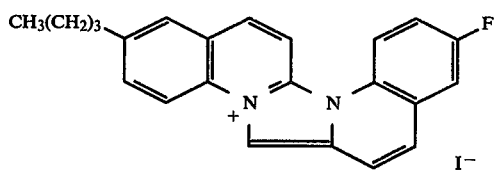

A mixture of 148 g. of 6-butylquinoline (J. Chem. Soc 1953, 2350), 32.2 g. of 6-fluoroquinaldine, 300 ml. of toluene and 101.5 g. of iodine is stirred for 30 minutes at 20°-25° C., then heated at 95°-100° C. for 6 days. The mixture is cooled, diluted with 400 ml. of toluene, and chilled to 0°-5° C. The precipitate is collected, washed with cold methanol and suspended in 500 ml. of methanol. The methanol suspension is treated with 20 ml. of hydrazine hydrate, then diluted with an equal volume of water. The solid 3-butyl-10-fluoroimidazo[1,2-a:3,4-a']diquinolin-15-ium iodide is collected by filtration, washed with water and dried; m.p. 275°-277° C.

In a similar manner, from the appropriate quinoline and quinaldine, the following product is obtained.

(a) 10-Fluoro-3-(1,1-dimethylethyl)imidazo[1,2-a3,4-a']diquinolin-15-ium Iodide; m.p. >360° C.

EXAMPLE 36

3-Cyclohexyl-10-fluoroimidazo[1,2-a:3,4-a']diquinolin-15-ium Iodide.

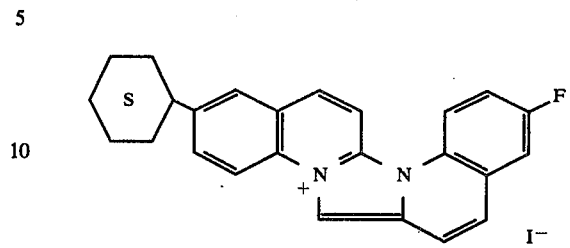

A mixture of 85.0 g. of 6-cyclohexylquinoline, 16.4 g. of 6-fluoroquinaldine, 150 ml. of toluene and 51.6 g. of iodine is stirred for 30 minutes at 20-25° C., then heated at 95°-100° C. for 6 days. The mixture is cooled, diluted with 300 ml. of chlorobenzene and treated dropwise with hydrazine hydrate until the dark-colored mixture becomes light tan. The precipitate is collected, washed with chlorobenzene and suspended in 400 ml. of cold methanol. The resulting solid 3-cyclohexyl-10-fluoroimidazo[1,2-a:3,4-a']diquinolin-15-ium iodide is collected by filtration and crystallized from dimethylformamide/methanol; m.p. ca 225° C.-235° C.

EXAMPLE 37

3,10-Difluoroimidazo[1,2-a:3,4-a']diquinolin-15-ium Iodide.

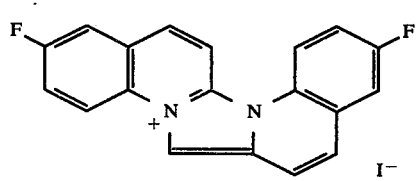

A mixture of 16.1 g. of 6-fluoroquinaldine, 58.9 g. of 6-fluoroquinoline, 70 ml. of chlorobenzene and 50.8 g. of iodine is stirred at 20°-25° C. for 1 hour, then heated at 95°-100° C. for 4 days. The precipitate is collected and suspended in 300 ml. of methanol. The methanol suspension is treated with 17 ml. of 85% hydrazine hydrate and the resulting solid 3,10-difluoroimidazo[1,2-a:3,4-a']diquinolin-15-ium iodide is collected by filtration; m.p. >360° C., after crystallization from methanol.

EXAMPLE 38

10-Fluoro-3-methylimidazo[1,2-a:3,4-a']diquinolin-15-ium p-Toluenesulfonate.

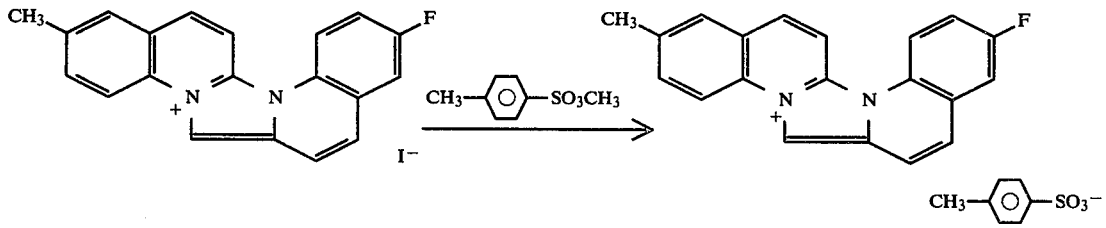

A mixture of 14.1 g. of 10-fluoro-3-methylimidazo[1,2-a:3,4-a']diquinolin-15-ium iodide and 12.3 g. of methyl p-toluenesulfonate in 115 ml. of dimethylformamide is stirred and heated at reflux for 20 minutes, then cooled. The precipitate of 10-fluoro-3-methylimidazo[1,2-a:3,4-a']diquinolin-15-ium p-toluenesulfonate is collected by filtration, washed with dimethylformamide, then with ethyl acetate, and dried; m.p. 287°–292° C.

In a similar manner, from the corresponding iodide salts, the following p-toluenesulfonate salts are obtained:
(a) 3-Fluoroimidazo[1,2-a:3,4-a']-diquinolin-15-ium p-Toluenesulfonate; m.p. 250°–252° C.
(b) 3,10-Difluoroimidazo[1,2-a']diquinolin-15-ium p-Toluenesulfonate; m.p. 247°–250° C.

What is claimed is:

1. A compound having the formula I:

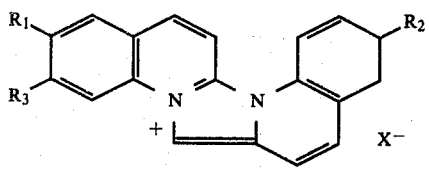

wherein

R$_1$ is hydrogen, lower alkyl, C$_4$–C$_6$ cycloalkyl, di(-lower alkyl)amino, 1-azetidinyl, 1-pyrrolidinyl, 1-piperidinyl, methyl-1-pyrrolidinyl, methyl-1-piperidinyl, 4-morpholinyl or 2,2-dimethylhydrazino;

R$_2$ is hydrogen, lower alkyl, lower alkylamino, di(-lower alkyl)amino, C$_4$–C$_6$ cycloalkylamino, lower alkoxy(lower alkyl)amino, 1-azetidinyl, 1-pyrrolidinyl, 1-piperidinyl, methyl-1-pyrrolidinyl, methyl-1-piperidinyl, hexahydro-1H-azepin-1-yl, 4-morpholinyl, benzylamino, N-methylbenzylamino or 2-phenylethylamino;

R$_3$ is hydrogen or methyl;

X is an anion;

with the proviso that at least one of R$_1$ and R$_2$ is other than hydrogen, lower alkyl or C$_4$–C$_6$ cycloalkyl; and with the further proviso that when R$_2$ is dimethylamino, at least one of R$_1$ and R$_3$ is other than hydrogen.

2. The compound according to claim 1 wherein R$_1$ is hydrogen, methyl, ethyl, n-butyl, t-butyl, dimethylamino, 1-pyrrolidinyl or methyl-1-piperidinyl; R$_2$ is hydrogen, methyl, ethyl, n-butyl, t-butyl, dimethylamino, methyl(butyl)amino, 1-pyrrolidinyl, 1-piperidinyl or methyl-1-piperidinyl; R$_3$ is hydrogen; and X is chloride, iodide or p-toluenesulfonate.

3. The compound according to claim 1 wherein R$_1$ is 1-pyrrolidinyl; R$_2$ is ethyl or t-butyl; R$_3$ is hydrogen, and X is chloride.

4. The compound according to claim 1 which is 10-methyl-3-(1-pyrrolidinyl)imidazo[1,2-a:3,4-a']diquinolin-15-ium chloride.

5. The compound according to claim 1 which is 3-dimethylamino-10-ethylimidazo[1,2-a:3,4-a]diquinolin-15-ium iodide.

6. The compound according to claim 1 which is 3-dimethylaminoimidazo[1,2-a:3,4-1']diquinolin-15-ium iodide.

7. The compound according to claim 1 which is 3-dimethylamino-10-methylimidazo[1,2-a:3,4-1']diquinolin-15-ium iodide.

8. The compound according to claim 1 which is 10-butyl-3-dimethylaminoimidazo[1,2-a:3,4-a']diquinolin-15-ium iodide.

9. The compound according to claim 1 which is 10-(1,1-dimethylethyl)-3-(1-pyrrolidinyl)imidazo[1,2-a:3,4-a']diquinolin-15-ium chloride.

10. The compound according to claim 1 which is 10-butyl-3-(1-pyrrolidinyl)imidazo[1,2-a:3,4-a']diquinolin-15-ium iodide.

11. The compound according to claim 1 which is 10-(dimethylamino)-3-methylimidazo[1,2-a:3,4-a']diquinolin-15-ium iodide.

12. The compound according to claim 1 which is 3-methyl-10-(1-pyrrolidinyl)imidazo[1,2-a:3,4-a']diquinolin-15-ium chloride.

13. The compound according to claim 1 which is 3-ethyl-10-(N-methylbutylamino)imidazo[1,2-a:3,4-a']diquinolin-15-ium iodide.

14. The compound according to claim 1 which is 3-(1,1-dimethylethyl)-10-(1-pyrrolidinyl)imidazo[1,2-a:3,4-a']diquinolin-15-ium iodide.

15. The compound according to claim 1 which is 3-butyl-10-(1-piperindinyl)imidazo[1,2-a:3,4-a']diquinolin-15-ium chloride.

16. The compound according to claim 1 which is 3,10-di-(dimethylamino)imidazo[1,2a:3,4-a']diquinolin-15-ium iodide.

17. The compound according to claim 1 which is 3,10-di-(1-pyrrolidinyl)imidazo[1,2-a:3,4-a']diquinolin-15-ium p-toluenesulfonate.

18. The compound according to claim 1 which is 3,10-di-(4-methyl-1-piperidinyl)imidazo[1,2-a:3,4-a']diquinolin-15-ium chloride.

19. The compound according to claim 1 which is 10(1-pyrrolidinyl)imidazo[1,2-a:3,4-a']diquinolin-15-ium iodide.

20. The compound according to claim 1 which is 10-dimethylamino-3-ethylimidazo[1,2-a:3,4-a']diquinolin-15-ium-p-toluenesulfonate.

21. The compound according to claim 1 which is 3-ethyl-10-(1-pyrrolidinyl)imidazo[1,2-a:3,4-a']diquinolin-15-ium iodide.

22. The compound according to claim 1 which is 10-ethyl 3-(1-pyrrolidinyl)imidazo[1,2-a:3,4-a']diquinolin-15-ium chloride.

23. The compound according to claim 1 which is 3-(1-pyrrolidinyl)imidazo[1,2-a:3,4-a']diquinolin-15-ium chloride.

24. A pharmaceutical composition for the treatment of fungal infections which comprises an effective amount of a compound having the formula I in claim 1 wherein X is a physiologically acceptable anion, together with an inert pharmaceutical carrier therefor.

25. The pharmaceutical composition according to claim 24 wherein, in the compound having the formula I in claim 1, R$_1$ is hydrogen, methyl, ethyl, n-butyl, t-butyl, dimethylamino, 1-pyrrolidinyl or methyl-1-piperidinyl; R$_2$ is hydrogen, methyl, ethyl, n-butyl, t-butyl, dimethylamino, methyl(butyl)amino, 1-pyrrolidinyl, 1-piperidinyl or methyl-1-piperidinyl; R$_3$ is hydrogen; and X is chloride or p-toluenesulfonate.

26. The pharmaceutical composition according to claim 24 wherein, in the compound having the formula I in claim 1, R$_1$ is 1-pyrrolidinyl; R$_2$ is ethyl or t-butyl; R$_3$ is hydrogen, and X is chloride.

27. The pharmaceutical composition according to claim 24 wherein the compound is 10-(1,1-dimethylethyl)-3-(1-pyrrolidinyl)imidazo[1,2-a:3,4-a']diquinolin-15-ium chloride.

28. The pharmaceutical composition according to claim 24 wherein the compound is 10-ethyl-3-(1-pyrrolidinyl)imidazo[1,2-a:3,4-a']diquinolin-15-ium chloride.

29. A method for treating fungal infections in mammals which comprises the administration of an effective amount of a compound having the formula I in claim 1 wherein X is a physiologically acceptable anion to mammals having fungal infections.

30. A method according to claim 29 wherein, in the compound having the formula I in claim 1, $R_1$ is hydrogen, methyl, ethyl, n-butyl, t-butyl, dimethylamino, 1-pyrrolidinyl or methyl-1-piperidinyl; $R_2$ is hydrogen, methyl, ethyl, n-butyl, t-butyl, dimethylamino, methyl(butyl)amino, 1-pyrrolidinyl, 1-piperidinyl or methyl-1-piperidinyl; $R_3$ is hydrogen; and X is chloride or p-toluenesulfonate.

31. A method according to claim 29 wherein, in the compound having the formula I in claim 1, $R_1$ is 1-pyrrolidinyl; $R_2$ is ethyl or t-butyl; $R_3$ is hydrogen, and X is chloride.

32. A method according to claim 29 wherein the compound is 10-(1,1-dimethylethyl)-3-(1-pyrrolidinyl)imidazo[1,2-a:3,4-a']diquinolin-15-ium chloride.

33. A method according to claim 29 wherein the compound is 10-ethyl-3-(1-pyrrolidinyl)imidazo[1,2-a:3,4-a']diquinolin-15-ium chloride.

* * * * *